United States Patent [19]

Kim et al.

[11] Patent Number: 5,482,712
[45] Date of Patent: Jan. 9, 1996

[54] GALENIC COMPOSITION

[75] Inventors: Moon H. Kim, Seoul; Chan K. Park, Anyang; Oh H. Kwon, Suwon, all of Rep. of Korea

[73] Assignee: Baekwha Co., Ltd., Kunsan, Rep. of Korea

[21] Appl. No.: 309,482

[22] Filed: Sep. 22, 1994

[30] Foreign Application Priority Data

Sep. 22, 1993 [KR] Rep. of Korea .................... 93-19327

[51] Int. Cl.$^6$ .................................................. A61K 35/78
[52] U.S. Cl. ........................ 424/195.1; 514/23; 514/811
[58] Field of Search .......................... 424/195.1; 514/23, 514/811

[56] References Cited

U.S. PATENT DOCUMENTS

| | | | |
|---|---|---|---|
| 4,806,354 | 2/1989 | Green | 424/154 |
| 5,204,369 | 4/1993 | Vallee et al. | 514/456 |
| 5,324,516 | 6/1994 | Pek et al. | 424/195.1 |

*Primary Examiner*—John W. Rollins
*Attorney, Agent, or Firm*—Oblon, Spivak, McClelland, Maier & Neustadt

[57] ABSTRACT

The galenic composition of this invention has been found to possess valuable pharmacological properties in the prevention and treatment of the aftereffects related to ingesting excessive amount of ethanol. The inventive composition decreases blood alcohol concentration by stimulating the alcohol metabolism and reduces the increased content of neutral fat in the blood due to alcohol intake. The composition comprises puerariae radix, phaseoli radiati semen, small red bean, crataegi fructus, malt, cnidii rhizoma, atractylodes rhizoma, cassiae semen, amomi semen, menthae folium and fructose. In the galenic composition of the present invention puerariae radix, phaseoli radiati semen, small red bean, crataegi fructus, malt, cnidii rhizoma, atractylodes rhizoma, cassiae semen, amomi semen, menthae folium and fructose is present preferably in the weight ratio of 20-50:20-50:20-50: 10-25:10-25:10-25:10-25:10-25:3-7:1-5:200-300, respectively.

9 Claims, 7 Drawing Sheets

GALENIC COMPOSITION

BACKGROUND OF THE INVENTION

1. Field of the Invention

The present invention relates to a galenic composition useful for alleviating the aftereffects due to an excessive intake of ethanol, commonly referred to as alcohol. More particularly, the present invention relates to a galenic composition useful for preventing and treating the aftereffects due to an excessive alcohol intake by stimulating alcohol metabolism, which comprises as the essential components puerariae radix, phaseoli radiati semen, small red bean, crataegi fructus, atractylodes rhizoma, cassiae semen, amomi semen, cnidii rhizoma, methae folium, malt and fructose.

2. Information Disclosure Statement

Ethanol is one of the drugs which have been most generally used for a long time in human history. As to the pharmacological activity of ethanol it has been reported that ethanol has an effect of preventing coronary artery diseases by reducing the plasma concentration of low density lipoprotein (LDL) and increasing the plama concentration of high density lipoprotein (HDL) but may induce harmful effects in the human body when a person drinks ethanol in an excessive amount for a short or long time. Short term toxic effects of ethanol may cause an accident due to CNS depression and various motor disturbance, depression of myocardial contraction, gastrointestinal disorders, and the like. In addition, it has been well known that the metabolite of ethanol is one of the substances causative of hangover symptoms such as headache, vomiting, etc. Long term effects from a history of excessive alcohol use may induce alcoholic hepatitis and related hepatic cirrhosis, psycho-neurological disorders such as cerebral damage, memory failure, sleeping disturbance, etc., fetal alcohol syndrome due to habitual drinking during the period of maternity, Wernicke encephalopathy, Korsakoff psychosis, polyneuritis, etc., due to malnutrition and vitamin deficiency, and the like. Today these undesirable toxic effects and after-effects due to excessive alcohol intake are treated by utilizing a popular remedy based on the administration of analgesics, agents for gastointestinal tract, high protein foodstuffs, etc.

However, although the use of such medicinal agents can alleviate the aftereffects of drinking alcohol, they have no effect of removing the basic cause of aftereffects through decomposition and excretion of alcohol component accumulated in the body, and therefore, are not helpful to remove or prevent various side effects and toxic effects due to aftereffects of drinking alcohol.

Thus, the present inventors have considered that in order to prevent and treat the aftereffects of excessive alcohol intake it will be necessary to use a medicinal agent which can rapidly decompose and excrete alcohol in blood to prevent any neurological toxic effects and also can regenerate cell tissues damaged by alcohol toxicity. Therefore, we have investigated natural crude drugs having such effects and then identified that the galenic composition of the present invention, as defined below, can exhibit an excellent effect for prophylaxis and treatment of the aftereffects due to an excessive alcohol intake. Then, now we have completed the present invention.

Therefore, it is an object of the present invention to provide a galenic composition useful for effectively preventing and treating the aftereffects due to an excessive intake of alcohol by stimulating alcohol metabolism and supplying the nutrition and vitality to the cells.

It is a further object of the present invention to provide a galenic composition useful for alleviating the aftereffects due to an excessive alcohol intake which comprises as essential components puerariae radix, phaseoli radiati semen, small red bean, crataegi fructus, cassiae semen, atractylodes rhizoma, amomi semen, cnidii rhizoma, menthae folium, malt and fructose.

Further, it is another object of the present invention to provide a process for preparing the galenic composition, as defined above.

The preceeding objects should be construed as merely presenting a few of the more pertinent and important features of the invention. Many other beneficial results can be obtained by applying the disclosed invention in a different manner or modifying the invention within the scope of the disclosure. Accordingly, other objects and a fuller understanding of the invention may be had by referring to the brief description of the drawings and the detailed description of the invention, below, which describe the preferred embodiments in addition to the scope of the invention defined by the claims considered in conjunction with the accompanying drawings.

BRIEF DESCRIPTION OF THE DRAWINGS

For a thorough understanding of the nature and objects of the invention, reference should be had to the following detailed description taken in connection with the accompanying drawings in which.

DISCLOSURE OF INVENTION

Figure 1:
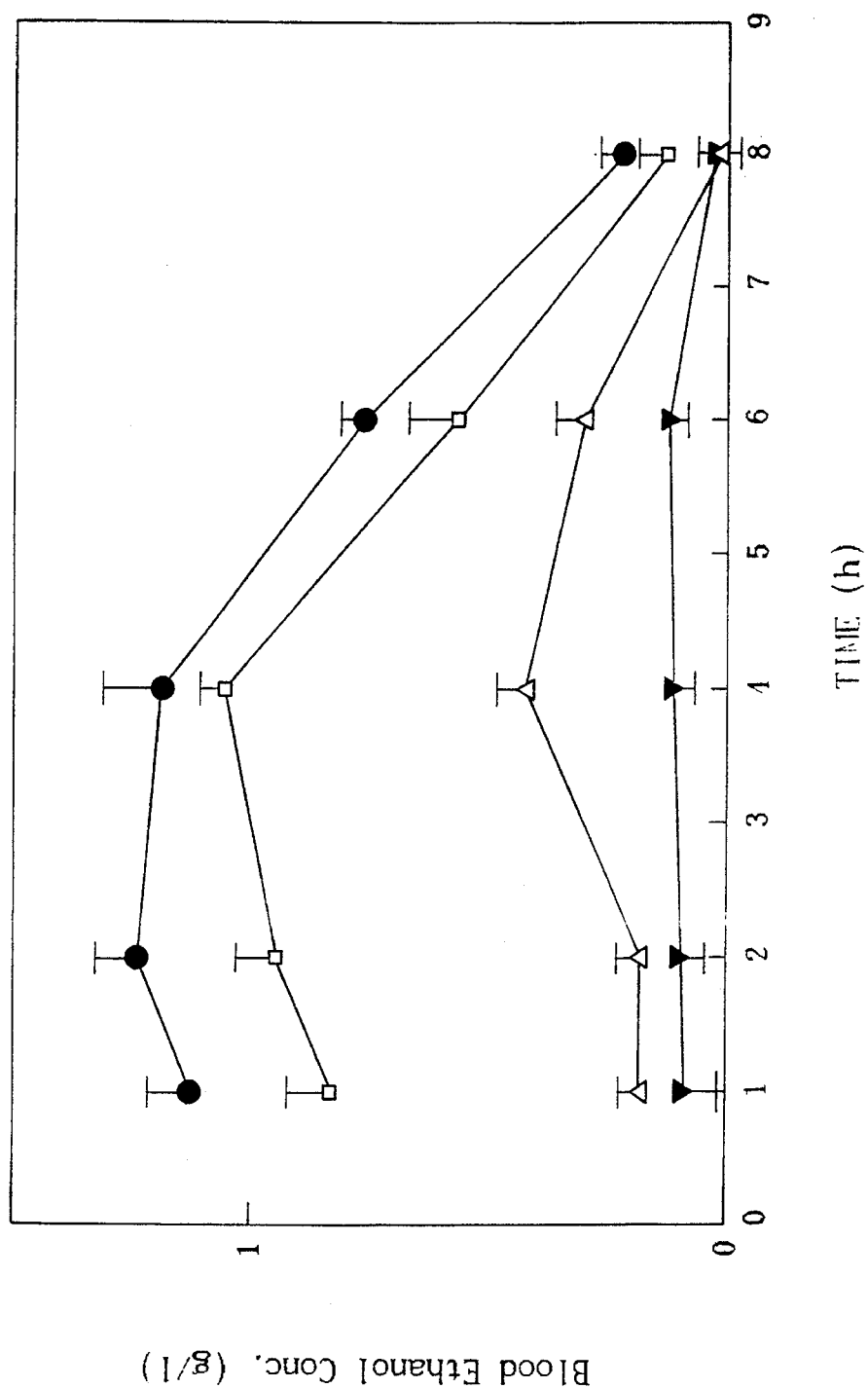
FIG. 1 is a graph showing the effect of the galenic composition according to the present invention on the blood ethanol concentration in rat depending on the administered dosage, as measured by Test 1 [-●-: control group, -■-: first test group, -▲-: second test group, -▼-: third test group]

In one aspect, the present invention is to provide a galenic composition useful for preventing and treating the aftereffects due to an excessive alcohol intake, which comprises as essential components puerariae radix, phaseoli radiati semen, small red bean, crataegi fructus, cassiae semen, atractylodes rhizoma, amomi semen, cnidii rhizoma, menthae folium, malt and fructose.

The galenic composition of the present invention can effectively prevent and treat the aftereffects due to an excessive alcohol intake by stimulating the alcohol decomposition and providing the nutrition and vitality to cells.

The galenic composition of the present invention can be prepared by extracting active constituents from plants with alcohol or purified water depending on their physico-chemical properties and/or by directly combining the components. In addition, the galenic composition of the present invention can include one or more substances selected from the group consisting of other conventional herb medicines and pharmaceutically acceptable excipients, in addition to the essential components as mentioned above.

The galenic composition of the present invention stimulates alcohol metabolism with alcohol metabolizing enzymes (alcohol dehydrogenase, aldehyde dehydrogenase) in the liver after alcohol intake to thereby reduce the level of alcohol in the blood at a faster rate than without administering the composition of the present invention and, therefore, reduces the toxic effects of alcohol. In addition, the galenic composition of the present invention can also reduce the increased content of neutral fat in the blood due to alcohol intake.

Although the pharmacological mechanism of the galenic composition of the present invention is not definitely established, it is estimated that the galenic composition of the present invention alleviates all the symptoms associated with the aftereffects of excessive drinking by increasing the activity of the enzymes responsible for alcohol metabolism, i.e. alcohol dehydrogenase (ADH) and aldehyde dehydrogenase (ALDH) to stimulate alcohol metabolism.

Puerariae radix which is used as one of the essential components in the galenic composition of the present invention is the decorticated root of Pueraria thunbergiana Bentham belonging to Leguminosae. The puerariae radix used in the present invention is in the form of a sliced irregular hexahedron having a surface area of about 5–10 $mm^2$ or a plate cutted lengthwise having a length of 20–30 cm, a width of 5–6 cm and a thickness of about 1 cm, of which the outer surface is tinted with a pale gray-yellow or gray-white color. Puerariae radix has been used in removing alcohol toxic effects and in alleviating thirst and gastrointestinal irritation.

Phaseoli radiati semen as another essential component used in the galenic composition of the present invention is the seed of Phaseolus radiatus Linne belonging to Leguminosae. In the present invention, the uniform and hard seed having a green-yellow color should be used. Phaseoli radiati semen has been used mainly for its antipyretic, detoxicating and diuretic effects.

As another essential component of the galenic composition of the present invention small red bean is the seed of Phaseolus angularis Wight or Phaseolus calcaratus Roxburgh, which belongs to Leguminosae. In the present invention, the full seed having a reddish-brown color should be used. Small red bean possesses diuretic, detoxicating, antiinflammatory and laxative effects.

Fructose is a monosaccharide ($C_6H_{12}O_6$) which is used for energy supply in diabetes and diabetes related conditions and detoxication in acute alcohol intoxication.

The galenic composition of the present invention can additionally contain adjuvant herb medicinal ingredients and auxiliary components such as sweetening agents, flavoring agents, and the like, in addition to the essential components, i.e. puerariae radix, phaseoli radiati semen, small red bean, crataegi fructus, cassiae semen, atractylodes rhizoma, amomi semen, cnidii rhizoma, menthae folium, malt and fructose.

More specifically, the galenic composition of the present invention can be prepared by extracting 20–50 parts of puerariae radix, 20–50 parts of phaseoli radiati semen, 20–50 parts of small red bean, 10–25 parts of crataegi fructus, 10–25 parts of malt, 10–25 parts of cnidii rhizoma, 10–25 parts of atractylodes rhizoma, 10–25 parts of cassiae semen, 3–7 parts of amomi semen and 1–5 parts of menthae folium with 50% spirit in an amount of 3 to 5 times with respect to the total weight of said herb medicines for about 12 hours and then with purified water in an amount of 2 to 4 times with respect to the total weight of said herb medicines for about 4 hours; filtering the extract; concentrating the filtrate to remove the alcohol component; subjecting the remaining extract to the centrifuge to remove the precipitate; and then adding 200–300 parts of fructose and an appropriate amount of purified water to the residue; and, if necessary, adding one or more components selected form the group consisting of pharmaceutically acceptable sweetening agents, flavoring agents, souring agents, and the like depending on the desired formulation, wherein the parts of the essential components are based on their weight. Said weight ratio of the essential components in the galenic composition of the present invention is the range of minimum amount to maximum amount both of which are identified as providing a sufficient effect for removing the aftereffects due to excessive alcohol drinking according to various comparative tests. Accordingly, if the amount of any of essential components is lower than the defined minimum amount or higher than the defined maximum amount, the synergistic activity with any other essential component is lowered or the desired sufficient effect of the galenic composition cannot be obtained.

In the galenic composition of the present invention, as a suitable sweetening agent one or more components selected from the group consisting of dextrose, saccharin, sodium saccharin, sorbitol, white sugar, sugar, lactose, honey, glucose and mannitol can be used. As a souring agent one or more components selected from the group consisting of lactic acid, citric acid, malic acid, succinic acid and other edible souring agents can be preferably used. As a flavoring agent one or more components selected from the group consisting of peppermint, spearmint, menthol and other flavoring agents which are harmless to the human body can be used.

Although the composition of the present invention may be used as it is, it can be formulated into various forms, such as liquid formulations, especially a water or alcohol extract, suspension, a gel, a solution, pills, tablets, capsules, powders or soft extract for easy oral administration. Such formulation can be manufactured by means of conventional methods known in the pharmaceutical technical field.

The present invention is more thoroughly explained through the following preparation example and tests. However, it should be understood that the present invention is not limited to these example and tests in any manner.

PREPARATION EXAMPLE

EXAMPLE 1

(A) 37.5 g of puerariae radix, 37.5 g of phaseoli radiati semen, 37.5 g of small red bean, 18.7 g of crataegi fructus, 18.7 g of malt, 18.7 g of cnidii rhizoma, 18.7 g of atractylodes rhizoma, 18.7 g of cassiae semen, 4.7 g of amomi semen and 2.4 g of menthae folium were introduced into a flask containing 800ml of 50% spirit and extracted for about 12 hours with heating at 80° to 100° C. Then, the mixture was filtered to obtain the extract. Then the residue was extracted again with 500 ml of purified water for 4 hours under heating in the same manner as above. The extracts were combined and then concentrated under reduced pressure to remove the alcohol component. The residue was mixed with 210 g of 95% fructose to prepare the concentrated extract of the galenic composition according to the present invention for removing the aftereffects of excessive alcohol intake.

(B) To the concentrated extract obtained in the above (A) were added appropriate amounts of conventional pharmacuetically acceptable sweetening agents, souring agents and flavoring agents. The mixture was adjusted with purified water to 2 liters to obtain the galenic composition according to the present invention in the form of a solution formulation.

TEST EXAMPLES

TEST 1

Effect of the galenic composition on blood alcohol concentration in rats 50 male rats weighing 150 to 200 g were fasted for 18 to 24 hours and then divided into four groups, i.e. the control group and the first, second and third test groups, each of which consists of 10 rats. The test groups were orally administered 2 g (the first test group), 4 g (the second test group) and 8 g (the third test group), per kg of body weight, of the extract powder prepared in Example 1(A) above dissolved in an appropriate amount of purified water and the control group was given the same volume of physiological saline. After one hour from the administration of the test sample, 3 g of alcohol per kg of body weight was administered per oral to each of the control and test groups. Bloods were collected from the rat tail after 1, 2, 4, 6 and 8 hours following alcohol administration. The collected blood was immediately treated to remove protein and then the alcohol concentration was determined. The change of alcohol concentration in blood over a period of time as measured is shown in FIG. 1.

From the result depicted in FIG. 1, it can be seen that in the test groups which are given the galenic composition of the present invention the alcohol absorption is slow and the blood alcohol concentration is significantly reduced over a period of time in comparison with the control group and exhibits a dose-dependent tendency. Therefore, the data obtained from the present test demonstrate that the galenic composition of the present invention stimulates alcohol metabolism.

TEST 2

Influence of the galenic composition on the triglyceride content. in serum

From the rats treated under the same condition as Test 1, the serum was separated after 0, 1, 2, 4, 6 and 8 hours following administration of alcohol and the content of triglyceride as a neutral fat in the serum was measured. As the test group the group which was given 4 g, per kg of body weight, of the galenic composition of the present invention was selected. The average value of the data obtained from 10 rats in each group was calculated. The obtained result is shown in FIG. 2.

Figure 2:
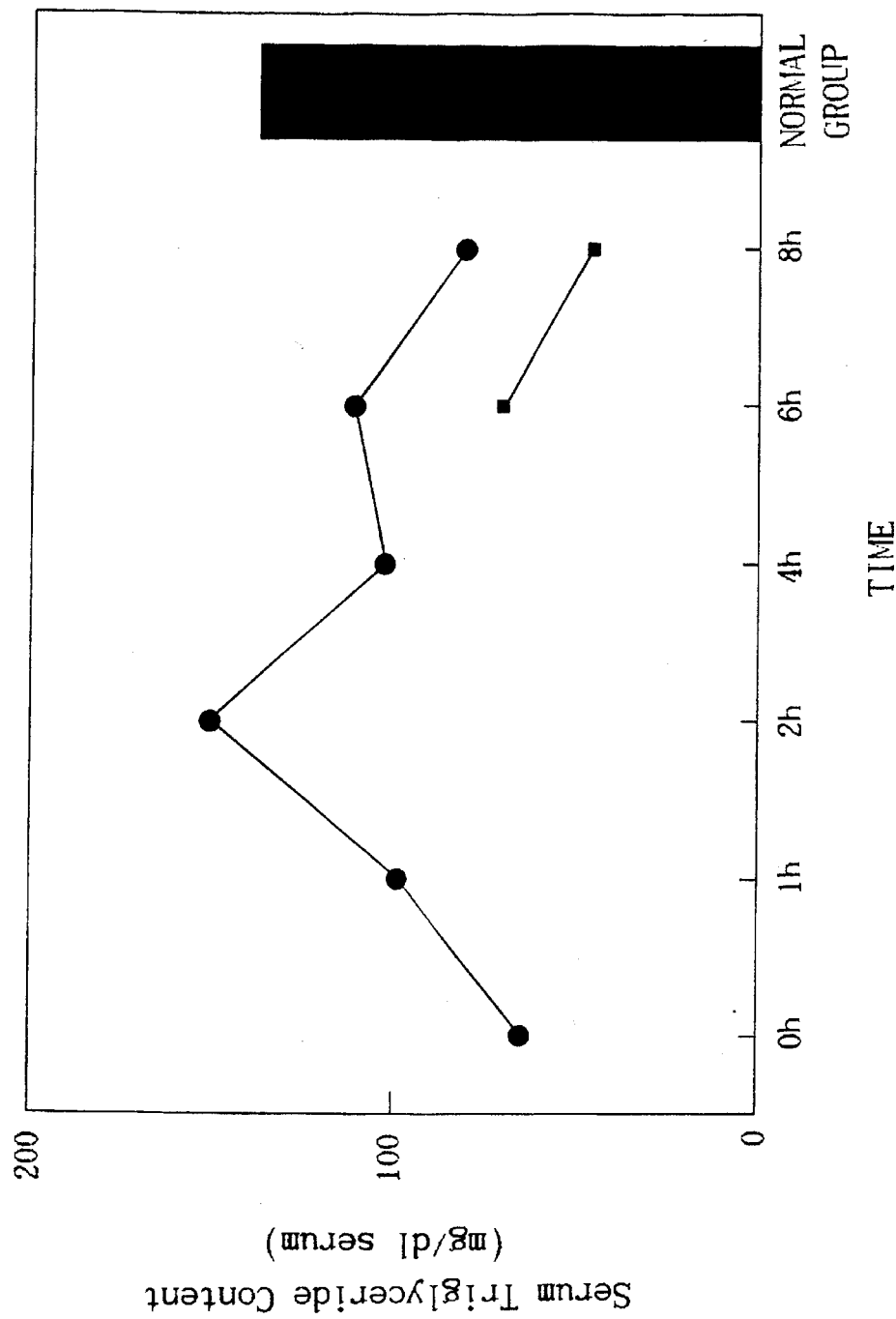
FIG. 2 is a graph showing the effect of the galenic composition according to the present invention on the triglyceride concentration in rat blood as measured by Test 2 [-●-: control group, -■-: test group]

From the result depicted in FIG. 2, it can be seen that in the test group which is given the galenic composition of the present invention the content of neutral fat in serum is greatly reduced in comparison with the control group. Therefore, the data obtained from the present test demonstrate that the galenic composition of the present invention can control the abnormal fat metabolism.

TEST 3

Assay for the activity of alcohol-metabolizing enzymes in rat liver

Male rats weighing 150 to 200 g were fasted for 18 to to 24 hours and then divided into the control group (to which alcohol is administered), the test group and the normal group, each of which consists of 7 rats. The test group was orally administered a solution of 4 g of powder prepared by Example 1(A) in purified water per kg of body weight and the control group and the normal group were given the same volume of physiological saline. After one hour from the administration of the test sample, 3 g of alcohol per kg of body weight was administered per oral to each of the control and test groups and the normal group was given the same volume of physiological saline.

After 0, 1, 2, 4 and 6 hours from the alcohol administration, rats from each group were sacrificed and the liver was removed from the rats and then washed with physiological saline solution. The washed liver was pulverized with a homogenizer and then subjected to the ultracentrifugation to obtain a cytoplasmic fraction and a mitochondrial fraction. The activity of alcohol dehydrogenase (ADH) in the cytoplasmic fraction and the activity of aldehyde dehydrogenase (ALDH) in the mitochondrial fraction were determined. The average values of activities of ADH and ALDH in each group are shown in FIGS. 3 and 4, respectively.

Figure 3:
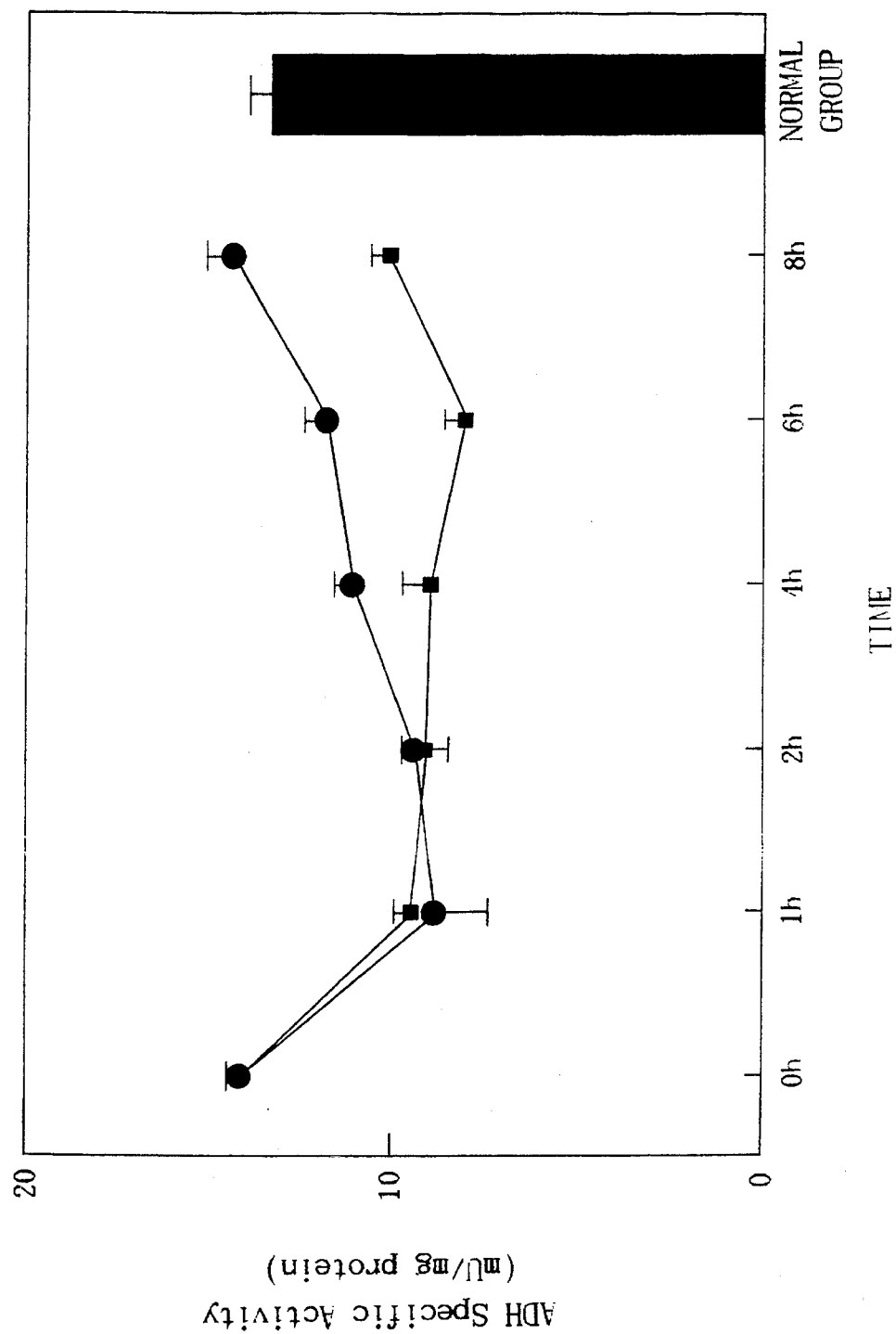
FIG. 3 is a graph showing the effect of the galenic composition according to the present invention on the activity of alcohol dehydrogenase (ADH) in rat liver as measured by Test 3 [-●-: test group, -■-: control group]
Figure 4:
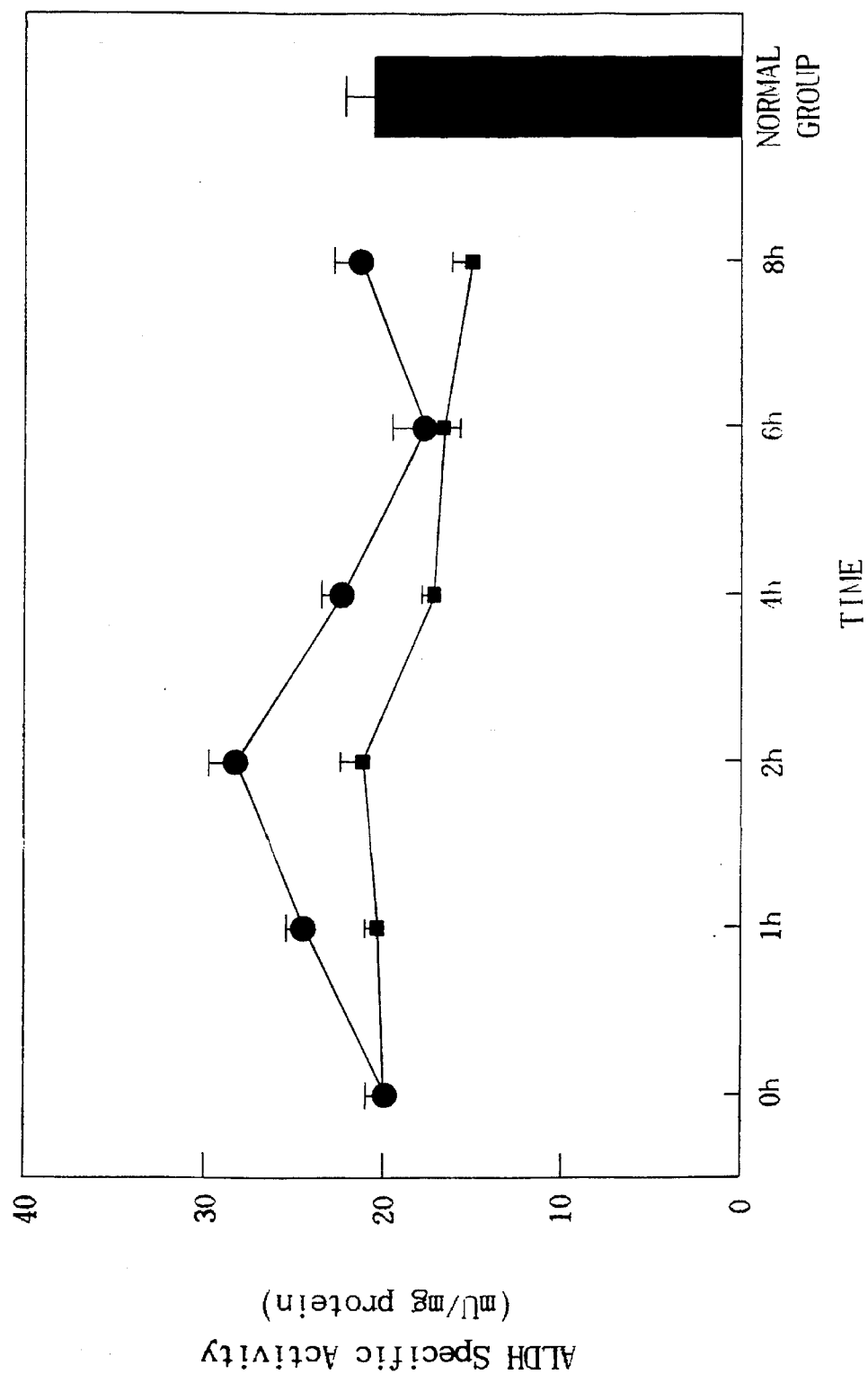
FIG. 4 is a graph showing the effect of the galenic composition according to the present invention on the activity of aldehyde dehydrogenase (ALDH) in rat liver as measured by Test 3 [-●-: test group, -■-: control group]

From the result depicted in FIGS. 3 and 4, it can be seen that the administration of the galenic composition according to the present invention results in an increase of ADH and ALDH activities in the rat liver, which were decreased by the alcohol intake, to the normal value or more. Therefore, it is considered that the decrease of alcohol concentration in blood after administration of the present galenic composition is caused by the stimulation of alcohol metabolism due to an increase of the activity of alcohol-metabolizing enzymes in the liver.

TEST 4

Influence of the galenic composition on the alcohol concentration in human blood The pharmacological effect of the galenic composition of the present invention was determined using 8 adult healthy men at the age of 40 to 60 years who have the body weight of the ideal body weight±10% and have neither disorder in liver and kidney function nor abnormality in scientific examination. Prior to initiation of the test, the experimenter sufficiently explained this experiment to the subjects and the test was initiated with the consent of the subjects. Prior to and after the test, for each subject scientific examination, electrocardiogram and basic blood chemical examination and urinary examination [test item: CBC (hemoglobin, hematocrit, leukocyte) , total protein/albumin, sGOT/sGPT, BUN, creatinine] were practiced. According to these examination the subject who are considered as suffering from disorder in liver and kidney function under the standard as mentioned below was excluded from this test.

[Standard of exclusion]
1. When the subject suffers from a disorder in liver function, i.e. when the sGOT/sGPT value as measured is twice or more the normal sGOT/sGPT value and the total protein/albumin value is beyond the normal range;
2. When the subject has a history of drug hypersensitivity and diseases in gastrointestinal tract, kidney, liver and heart;
3. When the subject suffers from alcoholism or medicinal poisoning or has a history thereof;
4. When the subject shows a serious acute toxic symptom even by a little alcohol intake;
5. When the subject takes a medicine within 2 weeks before initiation of the test; and
6. Other subject who is determined as being unsuitable by the experimenter.

According to the standard as mentioned above 8 normal subjects were selected. The subject was prohibited to take foodstuffs containing alcohol from 3 days before initiation of the test and fasted for 8 hours or more on the test day in order to practice the test. According to the random double-blind test, before 30 minutes from the administration of ethanol 70 ml of each of the test sample and the placebo filled in the cup in the same manner was administered to the subject and after one week as the washout period the cross test was praticed on each subject.

In the morning of the test day the subject was allowed to drink 1.2 g of ethanol per kg of body weight over 25 minutes. In order to minimize the influence of foodstuffs and drinking amount of water on the dynamic change of ethanol in the human body the subject was fasted for 4 hours after the ethanol administration and restricted to take the same kind of foodstuffs during the test. In addition, during the test the subject was prohibited to drink any luxury beverage except that water is provided restrictively in an amount of about 200 ml per 3 hours from 4 hours after the ethanol administration.

Blood was collected from a catheter filled with heparin (100 U/ml) and cannulated in antebrachial vein, in an amount of 2ml each time just before the ethanol administration and after 0.25, 0.5, 0.75, 1, 1.5, 2, 3, 4, 5, 6, 8, 10 and 12 hours from the start of ethanol administration. The collected blood was filled in a heparinized vacutainer tube and then used to measure the concentration of ethanol in blood. The result as measured is depicted in FIG. 5.

Figure 5:
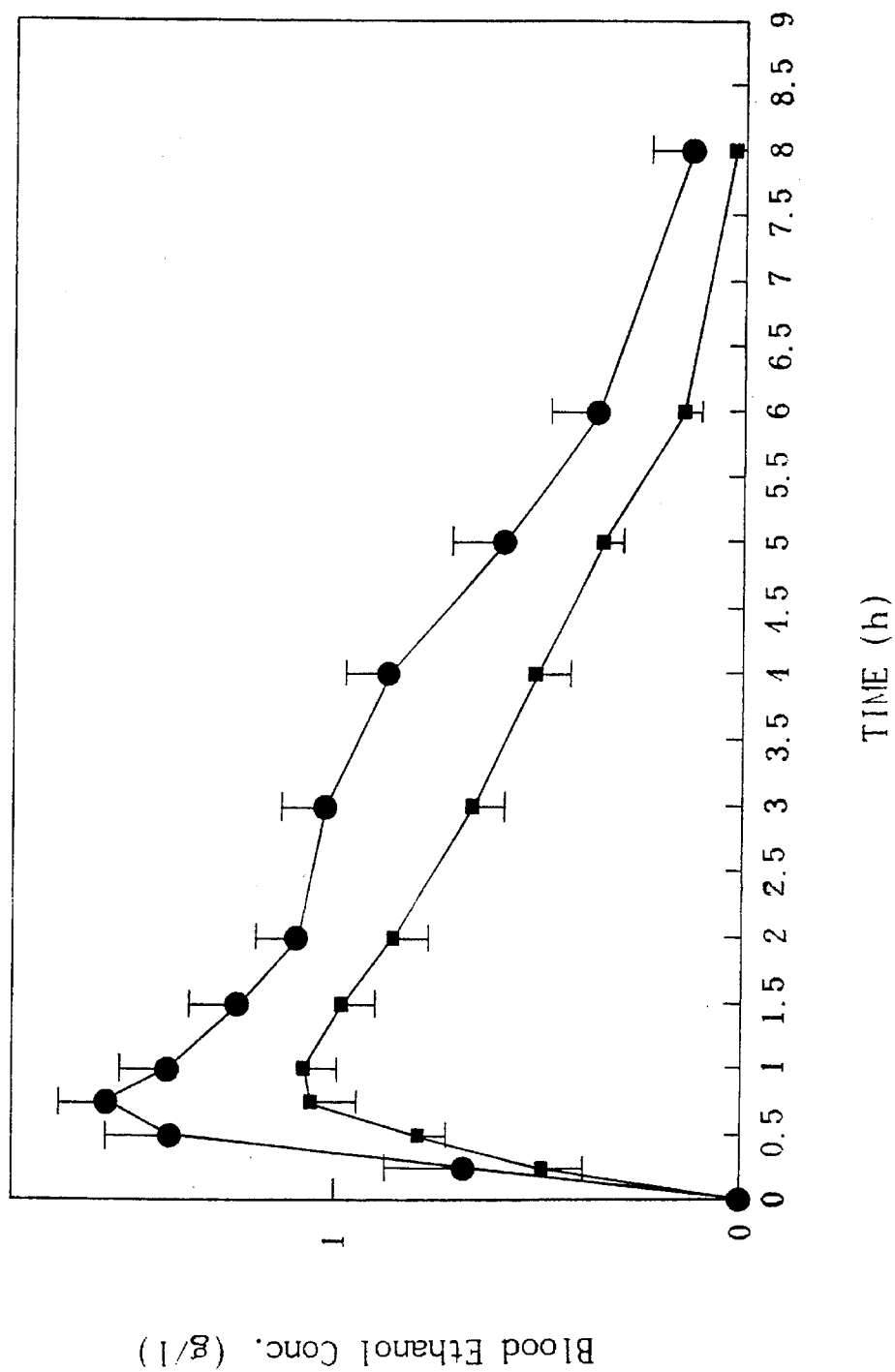
FIG. 5 is a graph showing the effect of the galenic composition according to the present invention on the ethanol concentration in human blood as measured by Test 4 [-●-: placebo group, -■-: test group ]

From the result depicted in FIG. 5, it can be seen that the administration of the galenic composition of the present invention significantly reduces the blood ethanol concentration in comparison with the administration of placebo.

TEST 5

Improvement in the aftereffects due to excessive alcohol intake by the galenic composition of the present invention 70ml of the solution of the galenic composition prepared in Example i(B) and the same amount of a placebo were administered to 8 adult healthy men at the interval of one week. After 30 minutes to one hour from the drug administration alcohol (1.2 g per kg of body weight) was administered to the subjects. Within 24 hours the subjective feelings and the objective symptoms were estimated according to the following standard and the average of the estimated values was calculated. The result is described in the following Table 1.

TABLE 1

Improvement in the after-effects by the galenic composition of the present invention

| | Headache | Vomiting (nausea) | Dyspepsia | Fatigue | Pallor |
|---|---|---|---|---|---|
| Placebo group | 1.4 | 1.8 | 1.3 | 1.6 | 1.2 |
| Test group | 0.6 | 0.6 | 0.4 | 0.4 | 0.5 |

Note)
Estimation standard:
1. Headache, Dyspepsia, Fatigue, Pallor
0: not appeared, 1: slight, 2: severe
2. Vomiting
0: not appeared, 1: slight nausea, 2: severe nausea, 3: vomiting

TEST 6

Effects of the galenic composition of the present invention on the change in cardiovascular system due to ethanol acute toxicity 70 ml of the solution of the galenic composition prepared in Example 1(B) and the same amount of a placebo were administered to 8 adult healthy men at the interval of one week. After 30 minutes to one hour from the drug administration alcohol (1.2 g per kg of body weight) was administered to the subjects. Within 24 hours the change in cardiovascular system was estimated. The result is depicted in FIGS. 6 and 7.

Figure 6:
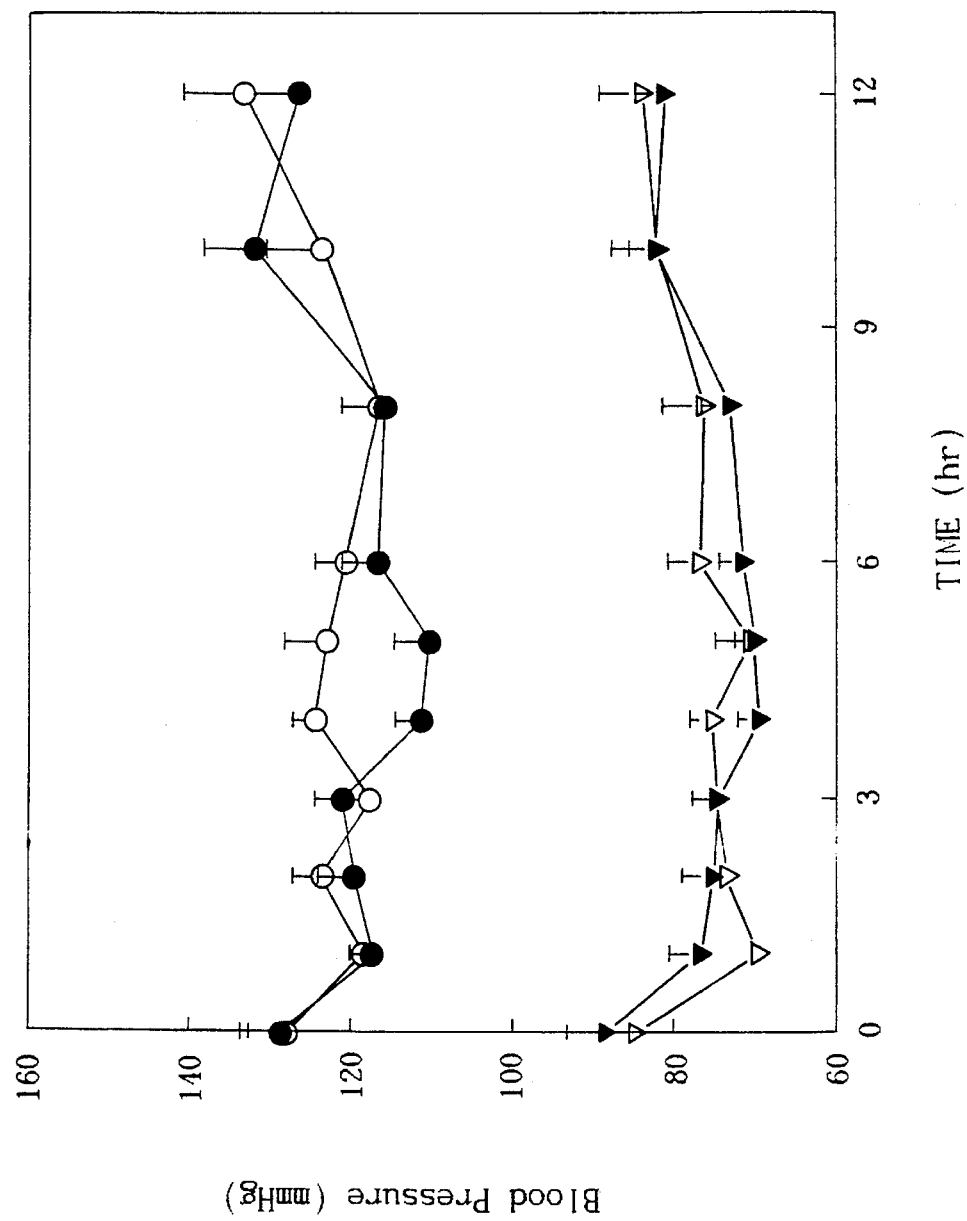
FIG. 6 is a graph showing the effect of the galenic composition according to the present invention on the systolic and diastolic blood pressures after alcohol is acutely administered to human, as measured by Test 6 [-○-: systolic blood pressure in the placebo group, -●-: systolic blood pressure in the test group, -▽-: diastolic blood pressure in the placebo group, -▼-: diastolic blood pressure in the test group]
Figure 7:
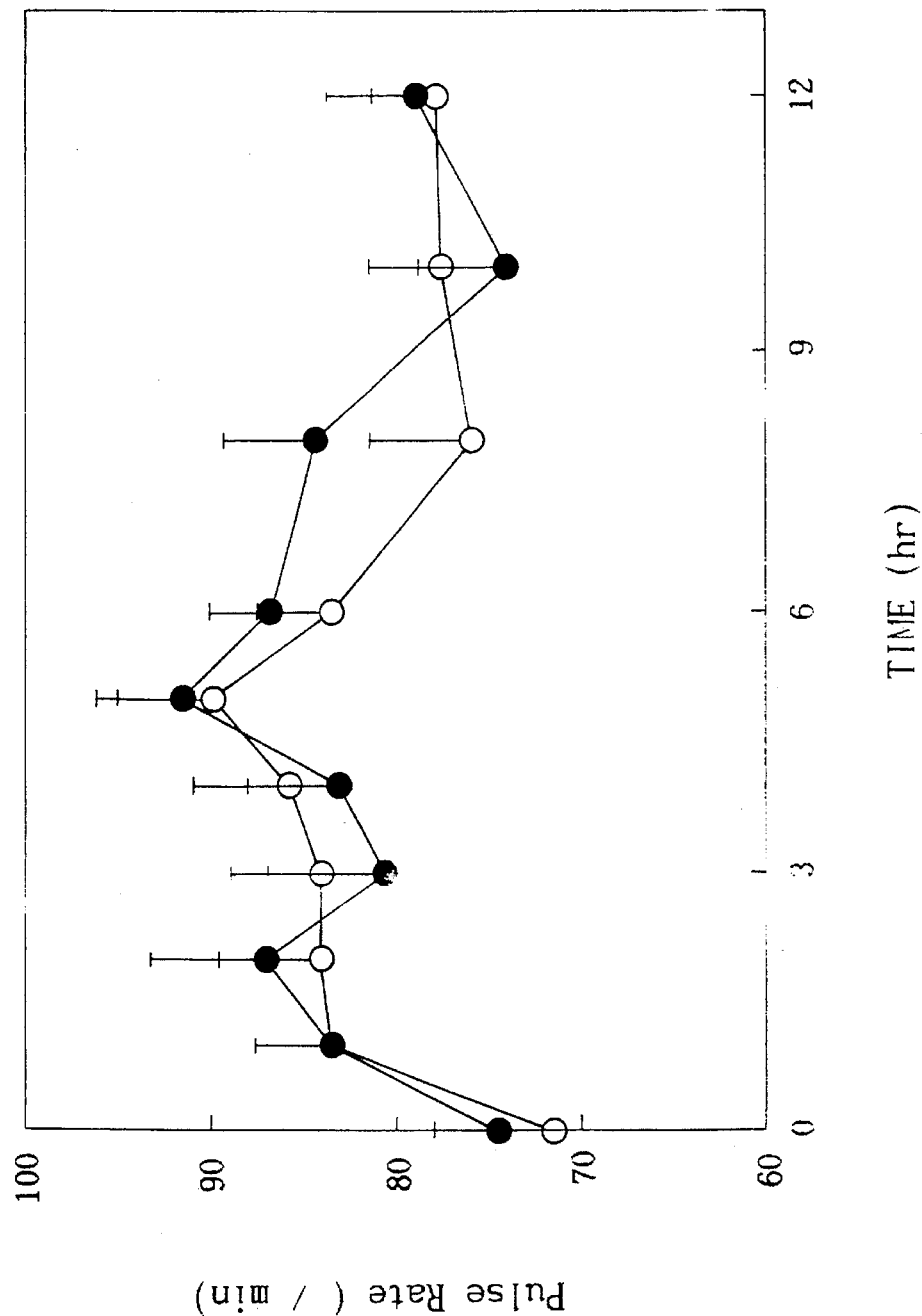
FIG. 7 is a graph showing the effect of the galenic composition according to the present invention on the pulse rate after alcohol is acutely administered to human, as measured by Test 6 [-○-: placebo group, -●-: test group].

As can be seen from the result depicted in FIGS. 6 and 7, the result obtained from the pre-administration of the galenic composition of the present invention is not significantly different from that of the pre-administration of placebo according to the statistical analysis of blood pressure and pulse rate over a period of time (systolic blood pressure $p=0.44$, diastolic blood pressure $p=0.71$, pulse rate $p=0.47$), except that at 4 hours following ethanol administration the systolic blood pressure in the case of the pre-treatment of the galenic composition of the present invention is $111.33 \pm 11.31$ mmHg which is significantly lower than $124.91 \pm 9.4$ mmHg in the case of placebo pre-treatment ($p<0.05$).

TEST 7

Acute Toxicity Test

The extract powder prepared in Example 1(A) was used as the test sample. For every dose of the test sample, ten of each of male and female weighing 20 to 25 g were used. Each amount of sample was dissolved in an appropriate amount of purified water and administered orally to each mouse in every morning under the condition of empty stomach. Thereafter, the clinical symptoms and vital conditions of each mouse were observed for 7 days. After the test is completed, each mouse was anatomized to observe the pathological condition by the macrography. The number of the survived mouse during the test is described in the following Table 2.

TABLE 2

| | Acute Toxicity in Mouse | | | | | |
|---|---|---|---|---|---|---|
| | Test sample amount (g/kg of body weight) | | | | | |
| | Control | 1 | 2 | 4 | 6 | 8 |
| Number of the survived mouse | | | | | | |
| Female | | | | | | |
| 1 Day | 10 | 10 | 10 | 10 | 10 | 10 |
| 2 Day | 10 | 10 | 10 | 10 | 10 | 10 |
| 3 Day | 10 | 10 | 10 | 10 | 10 | 10 |
| 4 Day | 10 | 10 | 10 | 10 | 10 | 10 |
| 5 Day | 10 | 10 | 10 | 10 | 10 | 10 |
| 6 Day | 10 | 10 | 10 | 10 | 10 | 10 |
| 7 Day | 10 | 10 | 10 | 10 | 10 | 10 |
| Lethality (%) | 0 | 0 | 0 | 0 | 0 | 0 |
| Male | | | | | | |
| 1 Day | 10 | 10 | 10 | 10 | 10 | 10 |
| 2 Day | 10 | 10 | 10 | 10 | 10 | 10 |
| 3 Day | 10 | 10 | 10 | 10 | 10 | 10 |
| 4 Day | 10 | 10 | 10 | 10 | 10 | 10 |
| 5 Day | 10 | 10 | 10 | 10 | 10 | 10 |
| 6 Day | 10 | 10 | 10 | 10 | 10 | 10 |
| 7 Day | 10 | 10 | 10 | 10 | 10 | 10 |
| Lethality (%) | 0 | 0 | 0 | 0 | 0 | 0 |

Since the sample of the galenic composition of the present invention is of a high viscosity, it was difficult to administer orally in an amount greater than 8 g per kg of body weight. At the possible maximum oral dose, all female and male mice survived and any remarkable clinical sign is not observed. The visible anatomical conditions after the test were normal.

From the above mentioned test results it can be determined that the galenic composition of the present invention exhibits an excellent effect for prophylaxis and treatment of aftereffects due to excessive alcohol intake without any side effect.

Although this invention has been described in its preferred form with a certain degree of particularity, it is appreciated by those skilled in the art that the present disclosure of the preferred form has been made only by way of example and that numerous changes in the details of the construction, combination and arrangement of parts may be resorted to without departing from the spirit and scope of the invention.

What is claimed is:

1. A galenic composition comprising:
   200–300 parts by weight fructose; and
   an alcohol or water extract of 20–50 parts by weight puerariae radix, 20–50 parts by weight phaseoli radiati semen, 20–50 parts by weight seeds of Phaseolus angularis Wight or Phaseolus Calcaratus Roxburgh, 10–25 parts by weight crataegi fructus, 10–25 parts by weight malt, 10–25 parts by weight cnidii rhizoma, 10–25 parts by weight atractylodes rhizoma, 10–25 parts by weight cassiae semen, 3–7 parts by weight amomi semen and 1–5 parts by weight menthae folium.

2. The galenic composition of claim 1 wherein the composition is in the form of suspension, gel or solution.

3. The galenic composition of claim 1, further comprising a pharmaceutically acceptable adjuvant or excipient.

4. The galenic composition according to claim 1, further including one or more components selected from the group consisting of: pharmaceutically acceptable sweetening agents, souring agents and flavoring agents.

5. A process for preparing the galenic composition which comprises the steps of:
   extracting herb medicines comprising 20–50 parts by weight puerariae radix, 20–50 parts by weight phaseoli radiati semen, 20–50 parts by weight seeds of Phaseolus angularis Wight or Phaseolus calcaratus Roxburgh, 10–25 parts by weight crataegi fructus, 10–25 parts by weight malt, 10–parts by weight cnidii rhizoma, 10–25 parts by weight atractylodes rhizoma, 10–25 parts by weight cassiae semen, 3–7 parts by weight amomi semen and 1–5 parts by weight menthae folium with 50% alcohol in an amount of 3 to 5 times with respect to the total weight of said herb medicines for about 12 hours under heating to form a mixture,
   filtering the mixture to form a first extract and a residue,
   extracting the residue with purified water in an amount of 2 to 4 times with respect to the total weight of said herb medicines for about 4 hours to form a second extract,
   combining the first and second extracts,
   concentrating the combined extracts to remove the alcohol component to form a remaining extract, and
   mixing the remaining extract with 200–300 parts by weight fructose.

6. The method of claim 5 wherein the resulting galenic composition is further diluted with purified water to obtain the composition in the form of a solution.

7. A method of stimulating alcohol metabolism in a person in need thereof, comprising administering to said person an alcohol metabolism stimulating amount of the galenic composition of claim 1.

8. The method of claim 7, wherein said person exhibits aftereffects of excess alcohol consumption.

9. A method of reducing the content of neutral fat in a person's blood due to alcohol intake, comprising administering to a person in need thereof, a neutral fat reducing amount of the galenic composition of claim 1.

* * * * *